United States Patent [19]
Adams et al.

[11] Patent Number: 5,925,685
[45] Date of Patent: *Jul. 20, 1999

[54] METHOD FOR CARRYING OUT HETEROGENEOUS CATALYSIS

[75] Inventors: John R. Adams; Thomas P. Hickey, both of Houston, Tex.

[73] Assignee: Catalytic Distillation Technologies, Pasadena, Tex.

[*] Notice: This patent is subject to a terminal disclaimer.

[21] Appl. No.: 08/943,212

[22] Filed: Oct. 6, 1997

Related U.S. Application Data

[60] Provisional application No. 60/031,025, Nov. 18, 1996.

[51] Int. Cl.[6] .............................. C07C 27/00; B01J 8/04
[52] U.S. Cl. ........................ 518/700; 518/713; 422/191; 422/195
[58] Field of Search .................... 518/700, 713; 422/191, 195

[56] References Cited

U.S. PATENT DOCUMENTS

| | | | |
|---|---|---|---|
| 4,302,356 | 11/1981 | Smith, Jr. ................. | 252/426 |
| 4,439,350 | 3/1984 | Jones, Jr. ................. | 502/527 |
| 4,443,559 | 4/1984 | Smith, Jr. ................. | 502/527 |
| 4,475,005 | 10/1984 | Paret ....................... | 568/697 |
| 4,847,430 | 7/1989 | Quang et al. ............. | 568/697 |
| 4,847,431 | 7/1989 | Nocca et al. ............. | 568/197 |
| 5,043,506 | 8/1991 | Crossland ................. | 585/449 |
| 5,057,468 | 10/1991 | Adams ..................... | 502/1 |
| 5,087,780 | 2/1992 | Arganbright .............. | 585/259 |
| 5,118,873 | 6/1992 | Smith, Jr. ................. | 568/697 |
| 5,189,001 | 2/1993 | Johnson .................... | 502/159 |
| 5,198,196 | 3/1993 | Jones, Jr. .................. | 422/219 |
| 5,262,012 | 11/1993 | Smith, Jr. ................. | 202/158 |
| 5,266,546 | 11/1993 | Hearn ...................... | 502/300 |
| 5,338,517 | 8/1994 | Evans, III et al. ......... | 422/191 |
| 5,348,710 | 9/1994 | Johnson et al. ........... | 422/211 |

*Primary Examiner*—Paul J. Killos
*Assistant Examiner*—Jafar Parsa
*Attorney, Agent, or Firm*—Kenneth H. Johnson

[57] ABSTRACT

Catalytic distillation reactions are improved by having an inert condensing component present in the reaction which is boiling and condensing within the reaction which washes the catalyst in the system and, in the case of gaseous reactants, occludes a portion of the reactants to facilitate the reaction without unduly high pressures. The inert condensing component is boiling at the conditions within the reactor and is taken overhead for condensation and return as reflux. The inert condensing component may occlude the gaseous reactants allowing for better contact with the catalyst and provides the benefits of concurrent reaction and distillation, for example, the reaction of CO and $H_2$ over a copper catalyst to produce methanol using propane as the inert condensing component.

18 Claims, 1 Drawing Sheet

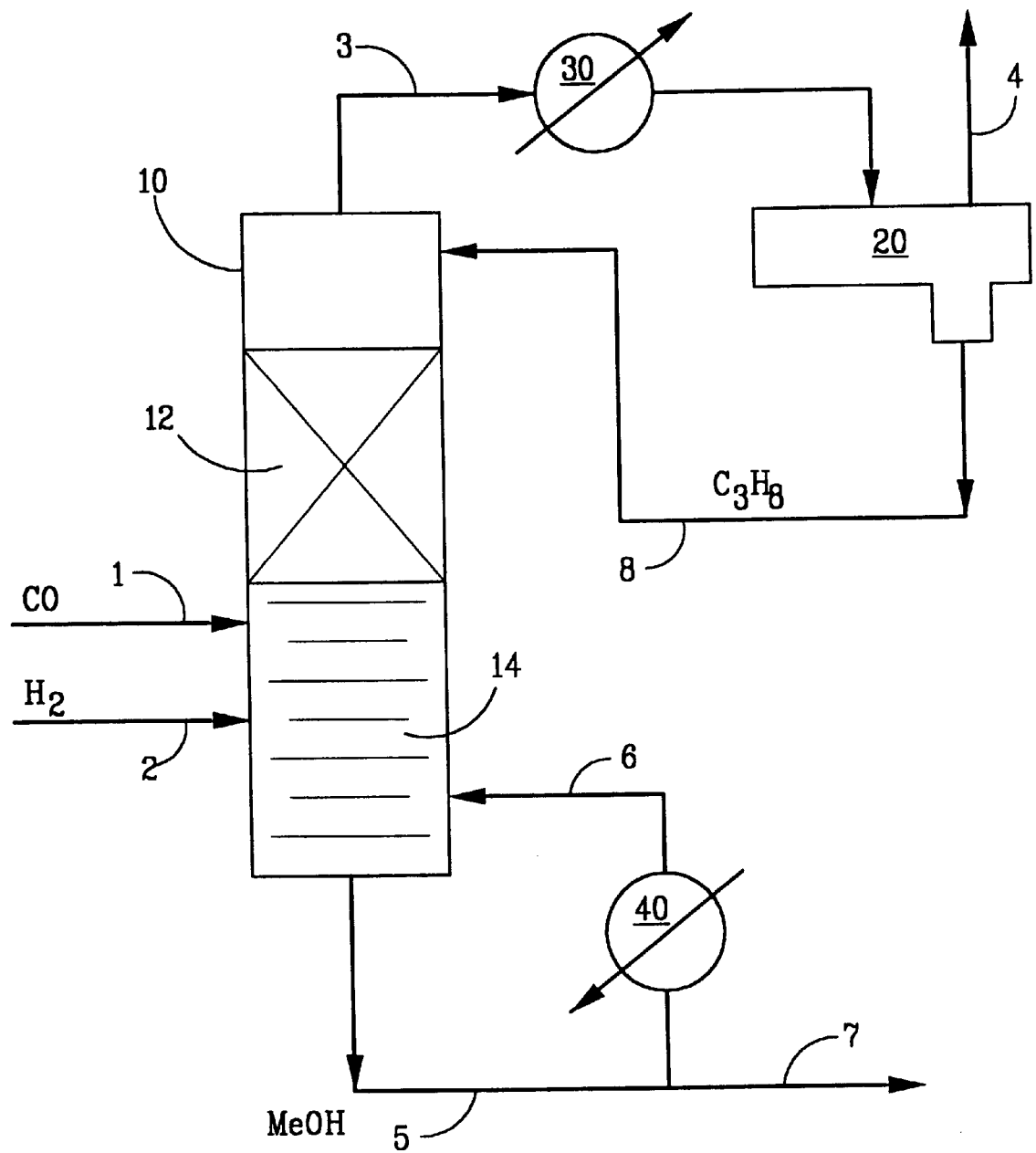

METHOD FOR CARRYING OUT HETEROGENEOUS CATALYSIS

This application claims the priority benefits of provisional application No. 60/031,025 filed Nov. 18, 1996.

BACKGROUND OF THE INVENTION

1. Field of the Invention

The present invention relates generally to reactions which are catalyzed by heterogeneous catalysts. More particularly the invention relates to the reaction of normally gaseous reactants in the presence of a heterogeneous catalyst. Most particularly the invention relates to the use of an inert component in a catalytic distillation column wherein the inert component is boiling and condensing.

2. Related Art

Over the years there have developed many methods of carrying out reactions in the presence of a solid heterogeneous catalyst. The most commonly used is probably the fixed bed downflow or trickle bed reactor. Also used is the upflow reactor which may have an ebullating bed if the flow rate is high enough. When the catalyst is fine and the reactants are gaseous a common method has been the fluidized bed. Similar to the fluidized bed is the slurry reactor wherein the solid catalyst is carried in one or more reactant streams. Finally there has arisen the reaction distillation column wherein the catalyst is disposed in a distillation column in a suitable form to act as a distillation structure. The final method has additional advantages in that the reaction products are separated from the reactants almost immediately upon formation by fractional distillation. This is particularly used in otherwise equilibrium limited reactions.

The use of catalytic distillation has been traditionally limited by the fact that one of the reactants must be a boiling liquid at the conditions inside the reactor. In the earlier catalytic distillation processes both reactants were fed to the reactor as liquids. More recently, U.S. Pat. No. 5,087,780 has shown that the catalytic distillation method is useful in a process wherein hydrogen is a reaction component.

SUMMARY OF THE INVENTION

Briefly the present invention is characterized as having an inert condensing medium or component, which is volatilized and condensed in a catalytic distillation column to provide continuous liquid contact of the inert component with the catalyst and may be described as a method for carrying out heterogeneously catalyzed reactions, comprising the steps of:
  (a) maintaining an inert condensing component in a distillation column reactor having a distillation reaction zone, said inert condensing component boiling at the conditions within said distillation column reactor;
  (b) feeding reactant to said distillation column reactor; and
  (c) concurrently in said distillation column reactor
    (i) boiling said inert condensing component and condensing and returning said inert condensing component to said distillation reaction zone;
    (ii) contacting said inert condensing component and said reactant with a solid particulate catalyst in said distillation reaction zone, and (
    iii) separating said product, said reactant and said inert condensing component by fractional distillation.

The present invention takes advantage of the characteristic traits of catalytic distillation while reacting normally gaseous reactants. The present invention contemplates utilizing an inert condensing medium or component for the reactants. The inert condensing component can be fed separately or intermingled with the gaseous feed.

BRIEF DESCRIPTION OF THE DRAWING

FIG. 1 is a flow diagram in schematic form of a process utilizing the present invention.

DESCRIPTION OF THE PREFERRED EMBODIMENTS

In one embodiment the distillation column reactor is operated at the boiling point of the inert condensing component with an overheads being taken and condensed and returned. The reflux of inert condensing component causes some of the evaporated inert condensing component to condense about the gaseous reactants to occlude the gaseous components and carry them to the active catalyst sites where they are present in a more dense form than usual.

Heretofore the problem has been that for some reactants the pressures necessary to produce a boiling liquid at the reaction temperature have been too high. Sometimes the reaction temperature may actually be above the critical temperature of the reactants. A solution has been found in the use of an inert condensing component which can be used as the boiling liquid. If the inert condensing component is judiciously selected it can have a boiling point much higher than the reactants and much lower or higher than the products allowing for easy separation within the distillation column reactor.

In some instances the inert condensing component may be solvent for the gaseous reactants, however, in some instances the inert condensing component is not known as a solvent for the reactants. The proposed mechanism for the present process does not depend on the chemical characteristics of solubility but on the physical characteristics of occlusion. If there is some degree of actual solubility of the gaseous reactants in the condensed inert component, this may enhance the results.

Preferably the inert condensing component is both vaporous and liquid within the column. As described above the condensation of the inert condensing component occludes a portion of the gaseous reactants and brings them in contact with the catalyst in the catalyst zone.

Although it is preferred the catalyst zone comprise catalytic distillation structures, catalyst in the catalyst zone may be positioned as shown in U.S. Pat. Nos. 4,847,431; 4,847,430; 4,475,005; 5,338,517; and 5,198,196; all of which are incorporated herein.

When the inert condensing component has a lower boiling point than the products, then the products can be easily separated in the distillation column reactor as bottoms. Additionally the fractional distillation will remove the products as they are formed which will improve the conversion in normally equilibrium limited reactions.

Therefore this aspect of the invention can be said to comprise:
  (a) maintaining an inert condensing component in a distillation column reactor having a distillation reaction zone, said inert condensing component boiling at the conditions within said distillation column reactor;
  (b) feeding a gaseous stream containing at least one reactant to a distillation column reactor, said reactant being at least partially occluded in said inert condensing component and said reactant being a vapor at the conditions within said reactor; and (c) concurrently in said distillation column reactor
   (i) boiling said inert condensing component and refluxing said inert condensing component such that a portion of said inert component is condensing in said distillation reaction zone;
   (ii) contacting said reactant and said inert condensing component with a solid particulate catalyst in said distillation reaction zone thereby reacting a portion of said reactant to form a product, and
   (iii) separating said product, said reactant and said inert condensing component by fractional distillation.

In another aspect of the present invention, wherein the reactants may be either gaseous or liquid within the distillation column reactor, but either reactants or products tend to foul the catalyst by forming deposits on the catalyst, the inert component condensate washes the catalyst and removes the deposits.

Finally, if the reactions are exothermic the boiling of the inert condensing component will remove heat as latent heat of vaporization which can be eventually removed in an overhead condenser. This latter feature is especially useful in temperature control because more heat of reaction only causes more boil up at a given pressure. Therefore the temperature can be simply controlled by the pressure. If the reaction requires heat input, a reboiler can supply the necessary energy.

The present invention takes advantage of the operating characteristics of catalytic distillation for normally gaseous reactions without operating at the pressures necessary to condense the gases. The advantages of catalytic distillation have become known over the past several years. The success of catalytic distillation lies in an understanding of the principles associated with distillation. First, because the reaction is occurring concurrently with distillation, the initial reaction product is removed from the reaction zone as quickly as it is formed. Second, because the reaction mixture is boiling, the temperature of the reaction is controlled by the boiling point of the mixture at the system pressure. The heat of the reaction simply creates more boil up, but no increase in temperature. Third, the reaction has an increased driving force because the reaction products have been removed and cannot contribute to a reverse reaction (Le Chatelier's Principle).

As a result, a great deal of control over the rate of reaction and distribution of products can be achieved by regulating the system pressure. Also, adjusting the through-put (residence time=weight hourly space velocity) gives further control of product distribution and degree of conversion. The temperature in the reactor is determined by the boiling point of the liquid mixture present at any given pressure. The temperature in the lower portions of the column will reflect the constitution of the material in that part of the column, which will be higher than the overhead; that is, at constant pressure a change in the temperature of the system indicates a change in the composition in the column. To change the temperature the pressure is changed. Temperature control in the reaction zone is thus controlled by the pressure; by increasing the pressure, the temperature in the system is increased, and vice versa. It can also be appreciated that in catalytic distillation as in any distillation there is both a liquid phase (internal reflux) and a vapor phase. Thus, the reactants are partially in liquid phase which allows for a more dense concentration of molecules for reaction, whereas, the concurrent fractionation separates product and unreacted materials, providing the benefits of a liquid phase system (and a vapor phase system) while avoiding the detriment of having all of the components of the reaction system continually in contact with the catalyst which would limit the conversion to the equilibrium of the reaction system components.

Another advantage, as noted above, is that a condensing liquid reactant occludes a gaseous reactant (such as hydrogen) which improves catalytic contact and lowers the necessary partial pressure of the occluded gaseous reactant.

A further advantage is the extra washing action of the refluxing inert condensing component on the catalyst, which are often fouled by the reactions.

Catalytic distillation structures and systems have been adequately described in the past as in commonly assigned U.S. Pat. Nos. 4,302,356; 4,439,350; 4,443,559; 5,507,468; 5,189,001; 5,262,012; 5,266,546; and 5,348,710; all of which are incorporated by reference. In particular the structure disclosed in above referenced U.S. Pat. No. 5,266,546 has been found useful when large amounts of gaseous components such as hydrogen are present.

Basically the patents disclose a solid particulate catalyst surrounded by or contained in a porous component to provide the requisite liquid and vaporous flows and catalyst contact without undue pressure drop.

The amount of inert condensing component present in the distillation column reactor is the amount required for an efficient distillation of that component.

Referring now to FIG. 1 a schematic flow diagram of a typical installation is shown for a reaction where a gaseous component is occluded in the inert condensing component. For illustration purposes a distillation column reactor is configured for the production of methanol from the reaction of carbon monoxide and hydrogen. A catalyst suitable for this reaction is copper in a reducing atmosphere of hydrogen.

Carbon monoxide is fed into distillation column reactor 10 via flow line 1 and hydrogen is fed via flow line 2. Both reactants are fed as gases and are gaseous at the conditions within the reactor. Since both reactants are gases they are fed below the distillation reaction zone 12 which contains the suitable catalyst in the form of a catalytic distillation structure.

A suitable condensing component in the case of the methanol synthesis reaction is propane. Since it is not consumed in the reaction but simply recycled it is fed as reflux via flow line 8. The condensing propane occludes a portion of the carbon monoxide and hydrogen and carries them to the active catalytic sites where they react to form methanol.

The methanol, having a higher boiling point than either of the reactants or the solvent, is fractionated out of the distillation zone into a stripping zone 14 which contains standard distillation structures such as sieve trays, bubble cap trays or inert packing. In the stripping zone 14 any propane or unreacted carbon monoxide or hydrogen is stripped back up into the distillation zone for further reaction. High purity methanol is withdrawn from the distillation column reactor as bottoms via flow line 5. A portion of the methanol may be circulated through reboiler 40 and flow line 6 to balance heat requirements. Product methanol is taken via flow line 7.

Vaporous propane is taken overhead via flow line 3 along with any unreacted carbon monoxide or hydrogen. The overheads are passed through partial condenser 30 where substantially all of the propane is condensed and the entire overheads passed to separator/collector 20. Any gaseous carbon monoxide and hydrogen is separated from the liquid propane in the drum 20 and removed via flow line 4 for recycle to the distillation column reactor if desired. The liquid propane is recycled to the top of the distillation column reactor as reflux via flow line 8. If propane is needed it can conveniently be added to the drum 20.

Utilizing a different catalyst the same system and reactants could be used to produce methane. The production of methane from the reaction of hydrogen and carbon monoxide is highly exothermic. To control the reaction a small volume of reactants would be used in relation to the inert component. In addition there would be no bottoms taken. Both inert component and product (methane) would be removed as overheads. The methane, being much lighter than the propane would be removed as a gas from the separator drum.

An example of the use of the inert condensing component to keep the catalyst clear is the isomerization reaction of butenes where the presence of methylacetlyene/propadiene (MAPD) impurity cause the isomerization catalyst, ie a zeolite to coke up. The use of cyclohexane as an inert condensing component in the reaction reduces the coking and substantially extends the catalyst use between regenerations.

The invention claimed is:

1. A method for carrying out heterogeneously catalyzed reactions, comprising the steps of:
   (a) maintaining an inert condensing component in a distillation column reactor having a distillation reaction zone, said inert condensing component boiling at the conditions within said distillation column reactor;
   (b) feeding reactant to said distillation column reactor, said reactant being a vapor at all times in said distillation column reactor; and
   (c) concurrently in said distillation column reactor
      (i) boiling said inert condensing component and condensing and returning said inert condensing component to said distillation reaction zone;
      (ii) contacting said inert condensing component and said reactant with a solid particulate catalyst in said distillation reaction zone to react a portion of said reactant and produce a reaction mixture containing unreacted reactant, inert condensing component and product wherein the reaction is carried out under conditions of temperature and pressure such that all of the reactant is a vapor, and
      (iii) separating said product, said reactant and said inert condensing component by fractional distillation.

2. A method for carrying out heterogeneously catalyzed reactions, comprising the steps of:
   (a) maintaining an inert condensing component in a distillation column reactor having a distillation reaction zone, said inert condensing component boiling at the conditions within said distillation column reactor;
   (b) feeding a gaseous stream containing at least one reactant to a distillation column reactor, a portion of said reactant being occluded in said inert condensing component and said reactant being a vapor at the conditions within said reactor; and
   (c) concurrently in said distillation column reactor
      (i) boiling said inert condensing component and condensing said inert condensing component and occluding a portion of said gaseous reactant in said inert component in said distillation reaction zone;
      (ii) contacting said inert condensing component and said occluded reactant with a solid particulate catalyst in said distillation reaction zone thereby reacting a portion of said reactant to form a reaction mixture containing product, unreacted reactant and inert condensing component wherein the reacting is carried out under conditions of temperature and pressure such that all of the reactant is a vapor, and
      (iii) separating said product, said reactant and said inert condensing component by fractional distillation.

3. The method according to claim 2 wherein said inert condensing component has a lower boiling point than said product and said product is removed from said distillation column reactor as bottoms.

4. The method according to claim 2 wherein said gaseous stream contains at least two reactants, said reactants being at least partially occluded in said inert condensing component and said reactants being vapors at the conditions within said reactor.

5. The method according to claim 2 wherein said inert condensing component has a higher boiling point than said product and said product is removed from said distillation column reactor as overheads.

6. The method according to claim 5 wherein said product is separated by distillation overhead from said inert condensing component and unreacted gases are removed from a separator drum.

7. The method according to claim 2 wherein said inert condensing component and any unreacted reactant are taken as overheads and said overheads are cooled to condense said inert component and said reactant is separated from said inert component in a separator drum.

8. The process according to claim 2 wherein said reactant is at least partially soluble in said inert condensing component.

9. The process according to claim 2 wherein said solid particulate catalyst is prepared as a catalytic distillation structure.

10. A method for carrying out heterogeneously catalyzed reactions, comprising the steps of:
    (a) feeding an inert condensing component as a liquid stream to a distillation column reactor having a distillation reaction zone, said inert condensing component boiling at the conditions within said distillation column reactor;
    (b) feeding a gaseous stream containing at least one reactant to a distillation column reactor, said reactant being at least partially soluble in said inert condensing component and said reactant being a vapor at the conditions within said reactor; and
    (c) concurrently in said distillation column reactor
       (i) boiling said inert condensing component and refluxing said inert condensing component such that a portion of said inert component is condensing in said distillation reaction zone;
       (ii) contacting said reactant and said inert condensing component with a solid particulate catalyst prepared as a catalytic distillation structure in said distillation reaction zone thereby reacting a portion of said reactant to form a reaction mixture containing product unreacted reactant and inert condensing component wherein the reacting is carried out under conditions of temperature and pressure such that all of the reactant is a vapor, and
       (iii) separating said product from said reactant and said inert condensing component by fractional distillation.

11. The method according to claim 10 wherein said inert condensing component has a lower boiling point than said product and said product is removed from said distillation column reactor as bottoms.

12. The method according to claim 10 wherein said gaseous stream contains two reactants, both of said reactants being at least partially occluded in said inert condensing component and said reactants being vapors at the conditions within said reactor.

13. The method according to claim 10 wherein said inert condensing component has a higher boiling point than said product and said product is removed from said distillation column reactor as overheads along with said inert component.

14. The method according to claim 10 wherein said product is separated from said inert condensing component by distillation overhead and unreacted gases are removed from a separator drum.

15. The method according to claim 10 wherein said inert condensing component and any unreacted reactant are taken as overheads and said overheads are cooled to condense said inert component and said reactant is separated from said inert component in a separator drum.

16. The method according to claim 10 wherein said gaseous reactant comprises hydrogen.

17. The method according to claim 16 wherein said gaseous reactant comprises carbon monoxide and the product is methanol.

18. The method according to claim 17 wherein said inert condensing component comprises propane.

* * * * *